United States Patent [19]

Gruneisen, III

[11] Patent Number: 4,969,213
[45] Date of Patent: Nov. 13, 1990

[54] VISORED CAP OR MASK AND FLEXIBLE BLANK THEREFOR

[76] Inventor: Albert Gruneisen, III, 1800 Spring Dr., Louisville, Ky. 40205

[21] Appl. No.: 329,295

[22] Filed: Mar. 27, 1989

[51] Int. Cl.$^5$ .............................................. A61F 9/00
[52] U.S. Cl. ............................................. 2/12; 2/171; 2/195; 2/206
[58] Field of Search ............... 2/12, 171, 171.1, 171.2, 2/172, 173, 173.5, 175, 177, 195, 196, 200, 206, 209.1, 209.3, 209.7

[56] References Cited

U.S. PATENT DOCUMENTS

| | | | |
|---|---|---|---|
| 727,173 | 5/1903 | Merrell | 2/206 |
| 766,419 | 8/1904 | Breck | 2/195 |
| 1,999,252 | 4/1935 | Mullendore | 2/171 |
| 2,019,028 | 10/1935 | Sternberg | 2/171 |
| 2,092,805 | 9/1937 | Jones | 2/12 |
| 2,293,436 | 8/1942 | Kelley | 2/12 |
| 2,594,906 | 4/1952 | Gardner | 2/200 |
| 2,787,791 | 4/1957 | Linney | 2/12 |
| 2,795,796 | 6/1957 | Ray | 2/206 |
| 2,964,757 | 12/1960 | Jarvis | 2/173 |
| 2,988,743 | 6/1961 | Wagenfeld | 2/12 |
| 3,041,628 | 7/1962 | Fish | 2/195 |
| 3,082,429 | 3/1963 | DeVillers | 2/195 |
| 3,184,757 | 5/1965 | Pennington | 2/12 |
| 4,027,340 | 6/1977 | Hadtke | 2/206 |
| 4,121,304 | 10/1978 | Cooper | 2/206 |
| 4,246,659 | 1/1981 | Lyons | 2/209.3 |
| 4,247,957 | 2/1981 | Rogers | 2/12 |
| 4,262,367 | 4/1981 | Herrin | 2/12 |
| 4,386,126 | 5/1983 | Turner | 2/12 |
| 4,468,818 | 9/1984 | Flannery | 2/195 |
| 4,670,910 | 6/1987 | Rosasco | 2/195 |
| 4,747,164 | 5/1988 | Foulke | 2/171 |
| 4,852,186 | 8/1989 | Landis | 2/196 |

FOREIGN PATENT DOCUMENTS

| | | | |
|---|---|---|---|
| 873083 | 7/1961 | United Kingdom | 2/200 |

Primary Examiner—Werner H. Schroeder
Assistant Examiner—Diana L. Biefeld
Attorney, Agent, or Firm—Jon C. Winger

[57] ABSTRACT

A disposable visored cap or mask to be worn during outdoor or indoor activities to shade the wearer's eyes from the light, or as a cap or mask representing a club mascot or displaying advertisements. The visored cap, and blank therefor, is fabricated of a flexible material such as paper, cardboard, and the like. The blank has a first end edge, a second end edge, an arcuate fold line spaced from the first end edge defining a visor therebetween, and a straight fold line between the first end edge and second end edge defining an intermediate portion between the straight fold line and arcuate fold line and defining a front panel between the straight fold line and second end edge. To fold the blank to form the cap or mask, the intermediate portion is folded upwardly about the straight fold line to overlay the front panel, and the visor is folded in the opposite direction or downwardly about the arcuate fold line to project outwardly from the front panel. In a further embodiment, a cutout portion is formed through the blank centered on the length first fold line and centered on a bisecting centerline of the first fold line so that when the blank is folded to form the cap or mask and the cutout portion removed, coinciding notches are formed in the intermediate portion and front panel centered on the bisecting centerline of the visor for receiving the bridge of the nose of the person wearing the cap so that the the cap can be worn over the wearer's face as a mask.

15 Claims, 2 Drawing Sheets

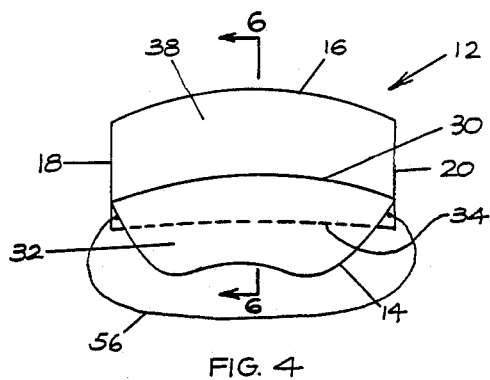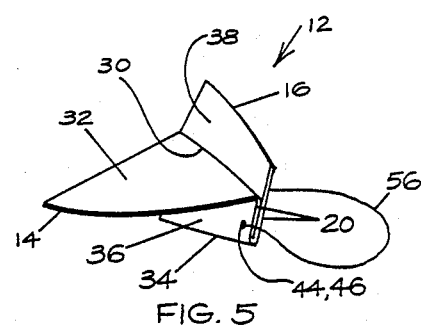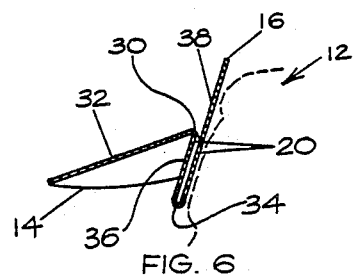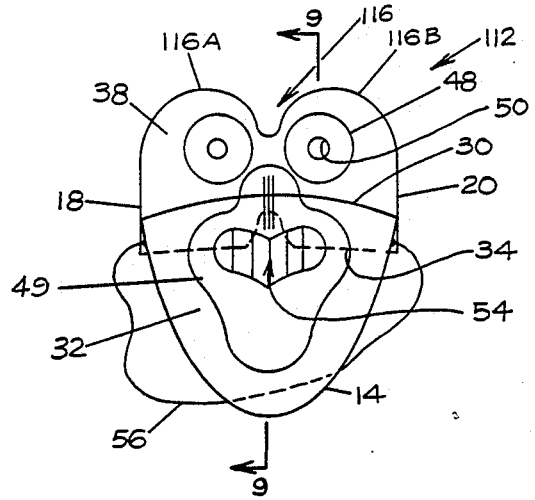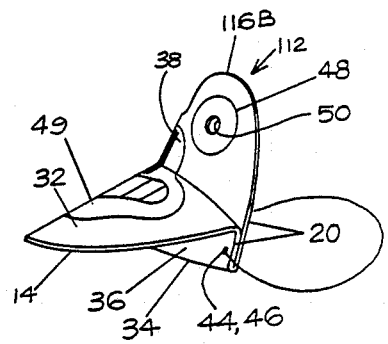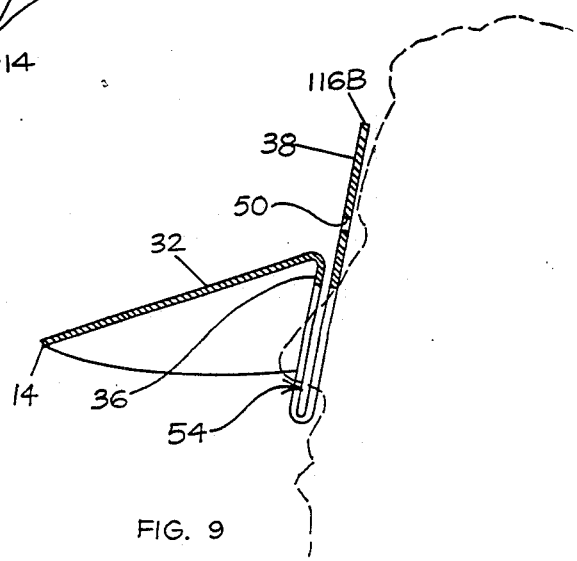

VISORED CAP OR MASK AND FLEXIBLE BLANK THEREFOR

BACKGROUND OF THE INVENTION

The invention relates to visored caps and the like, such as masks, and a blank for forming the cap of a single sheet of flexible material.

An object of the present invention is to provide a visored cap and the like, and blank therefor which is inexpensive to make and, therefore, is disposable even after one use. Thusly, the visored cap or mask can be distributed for free, or sold at a minimum cost to the purchaser which makes it ideal for advertisers to promote their product or service, or promote a sporting event, or to fans attending a sporting event to show their team loyalty.

Visor caps made of a blank of flexible sheet material are, per se, known. Various examples of such caps and blanks are shown in U.S. Pat. No. 1,401,758 issued on Dec. 27, 1921 to W. A. Carleton, U.S. Pat. No. 2,092,805 issued on Sept. 14, 1937 to J. P. Jones, U.S. Pat. No. 2,293,436 issued on Aug. 18, 1942 to J. MM. Kelley, U.S. Pat. No. 2,545,097 issued on Mar. 13, 1951 to G. R. Lucas, U.S. Pat. No. 2,787,791 issued on Apr. 9, 1957 to A. T. Linney, U.S. Pat. No. 2,988,743 issued on June 30, 1961 to G. B. Wagenfeld, U.S. Pat. No. 4,262,367 issued on Apr. 21, 1981 to Lenny Herrin, and U.S. Pat. No. 4,670,910 issued on June 9, 1987 to Leroy Rosasco.

SUMMARY OF THE INVENTION

In one embodiment, the present invention provides a flexible blank for a visored cap comprising a first end edge; a second end edge opposite the first edge; the bisecting centerline of the first end edge being in alignment with the bisecting centerline of the second end edge, and each of the terminate ends of the first end edge being in alignment with a different one of the terminate ends of the second end edge; first and second side edges, the first side edge interconnecting one of the terminal ends of the first end edge and the aligned one of the terminal ends of the second end edge, and the second side edge interconnecting the other one of the terminal ends of the first end edge and the aligned other one of the terminal ends of the second end edge; an arcuate fold line extending between the first and second side edges convexly facing the first end edge with the bisecting centerline of the arcuate fold line in alignment with the bisecting centerline of the first end edge; and, a straight fold line located between the second end edge and the first fold line extending between the first and second side edges, and the bisecting centerline of the straight fold line being in alignment with the bisecting centerlines of the first arcuate end edges, the second end edge, and the arcuate fold line.

In another embodiment, the present invention provides a visored cap to be worn on a person's head comprising a continuous flexible blank having a first and edge, a second end edge opposite the first end edge wherein the bisecting centerline of the first end edge is in alignment with the bisecting centerline of the second end edge, and each of the terminating ends of the first convex arcuate end edge being in alignment with a different one of the terminal ends of the second end edge, first and second side edges, the first side edge interconnecting one of the terminal ends of the first end edge and aligned one of the terminal ends of the second end edge, and the second side edge interconnecting the other one of the terminal ends of the first end edge and the aligned other one of the terminal ends of the second end edge, an arcuate fold line extending between the first and second side edges convexly facing the first arcuate end edge with the bisecting centerline of the arcuate fold line in alignment with the bisecting centerline of the first end edge, the arcuate fold line and first end edge cooperating to define a visor portion between the arcuate fold line and the arcuate first end edge and a straight fold line located between the second end edge and the first fold line extending between the first and second side edges, and bisecting centerline of the straight fold line being in alignment with the bisecting centerlines of the first arcuate end edges, the second end edge, and the arcuate fold line, the straight fold line and arcuate fold line cooperating to define an intermediate portion, and the straight fold line and second end edge cooperating to define a front panel portion wherein the intermediate portion is folded upwardly about the straight fold line to overlay outside surface of the front panel portion and the visor portion is folded downwardly about the arcuate fold line to form a curved visor projecting outwardly from the outside surface of the front panel.

BRIEF DESCRIPTION OF THE DRAWINGS

A better understanding of the invention will be had upon reference to the following description in conjunction with the appended drawings wherein like numerals refer to like parts throughout the several views and in which:

FIG. 4 is a front view of a visored cap of the present invention;

FIG. 5 is a side view of the visored cap of FIG. 4;

FIG. 6 is a cross-sectional side view as seen in the direction of arrows 6—6 in FIG. 4; and, FIG. 7 is a front view of a visor cap formed of the blank of FIG. 3;

FIG. 8 is a cross-sectional side view as seen in the direction of arrows 8—8 in FIG. 7; and FIG. 9 is a cross-sectional side view of the cap of FIG. 8 worn as a mask.

DETAILED DESCRIPTION OF THE EMBODIMENTS

Figure 1:
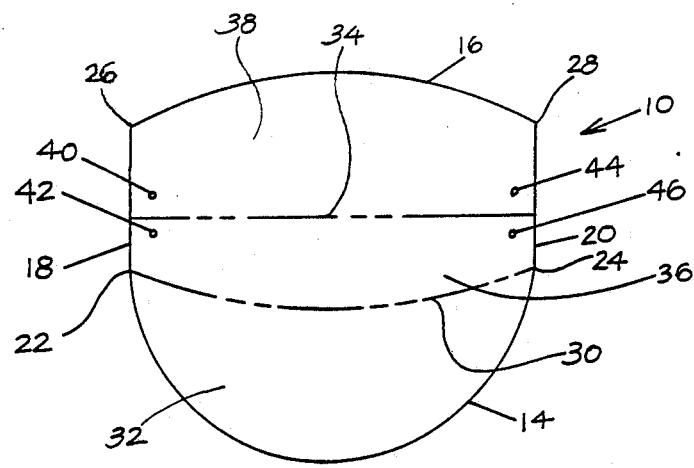
FIG. 1 is a plan view of one embodiment of a novel blank of the invention from which a visored cap of the present invention is formed.
Figure 2:
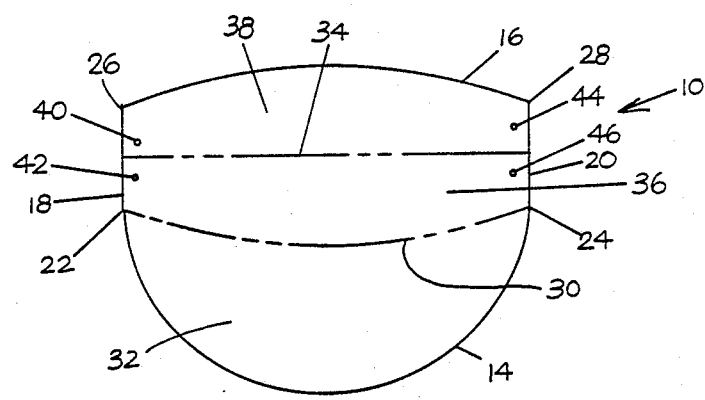
FIG. 2 is a plan view of another embodiment of a novel blank of the invention.

With reference to FIGS. 1 and 2, there is a flexible blank, generally denoted as the numeral 10, for forming a visor cap 12 (see FIGS. 4–6). The blank 10 is a sheet of flexible material such as paper, cardboard, plastic and the like. The blank 10 comprises a first end edge 14, a second end edge 16 opposite the first end edge 14, a first side edge 18, and a second side edge 20. As shown in FIGS. 1 and 2, the first end edge 14 is a convex arcuate edge and the second end edge 16 is also a convex arcuate edge. The first and second arcuate end edges 14 and 16 concavely face each other, an imaginary bisecting centerline of the first end edge 14 is in alignment with the bisecting centerline of the second end edge 16, and the terminal ends 22, 24 of the first end edge 14 are each in alignment with a different one of the terminating ends 26, 28 of the second end edge 16. The first side edge 18 interconnects one of the terminal ends 22 of the first end edge 14 and one of the aligned one of the terminal ends 26 of the second end edge 16. The second side edge 20 interconnects the other one of the terminal ends 24 of the first end edge 14 and the aligned other one of the terminal ends 28 of the second end edge 16. As shown, the first and second side edges 18 and 20 are straight edges, parallel to each other and parallel to the aligned imaginary bisecting centerlines of the first and second end edges 14, 16. An arcuate fold line 30 extends between the first and second side edges 18, 20 convexly facing the first end edge 14 with an imaginary bisecting centerline of the arcuate fold line 30 in alignment with the imaginary bisecting centerline of the first end edge 14 and the imaginary bisecting centerline of the second end edge 16. The space between the arcuate fold line 30 and the first end edge 14 defines a visor 32 of the cap 12. A straight fold line 34 is located between the second end edge 16 and the arcuate fold line 30 extending between the first and second side edges 18, 20 with an imaginary bisecting centerline of the straight fold line 34 in alignment with the bisecting centerlines of the first arcuate end edge 14, the second end edge 16, and the arcuate fold line 30. The space between the arcuate fold line 30 and straight fold line 34 defines an intermediate portion 36 of the cap 12, and the space between the straight fold line 34 and second end edge 16 defines a front panel 38 of the cap 12. As shown in FIGS. 1 and 2, the intersections of the arcuate fold line 30 and the first side edge 18 coincides with the intersection of one of the terminal ends 22 of the first end edge 14 and the first side edge 18. Similarly, the intersection of the straight fold line 34 and the second side edge 20 coincides with the intersection of the other one of the terminal ends 24 of the first end edge 14 and the second side edge 20.

With continued reference to FIGS. 1 and 2, a first pair of apertures 40, 42 and a second pair of apertures 44, 46 are formed through the blank 10. The first pair of apertures 40, 42 are located proximate the first side edge 18 with the aperture 40 being spaced to one side of the straight fold line 34 and the aperture 42 being spaced to the opposite side of the straight fold line 34. The other pair of apertures 44, 46 are located proximate the second side edge 20 with the aperture 44 being spaced to one side of the straight fold line 34 and the aperture 46 being spaced to the opposite side of the straight fold line 34. A centerline extending between one of the apertures 40 of the first pair and one of the apertures 44 of the second pair on one side of the straight fold line 34 is parallel to the straight fold line 34 and a centerline extending between the other one of the apertures 42 of the first pair and the other one of the apertures 46 of the second pair on the other side of the straight fold line 34 is parallel to the straight fold line 34.

Comparing FIGS. 1 and 2, essentially the only difference therebetween are dimensional. In the embodiment of FIG. 1, the intersections of the terminal ends 26, 28 of the second end edge 16 with the first and second side edges 18, 20, respectively, are spaced a greater distance from the straight fold line 34 than the distance by which the intersections of the terminal ends 22, 24 of the first end edge 14 with the first and second side edges 18, 20, respectively, are spaced from the straight fold line 34. By contrast, in the embodiment of FIG. 2, the intersections of the terminal ends 26, 28 of the second end edge 16 with the first and second side edges 18, 20, respectively, are spaced from the straight fold line 34 by a distance equal to the distance by which the intersections of the first end edge 14 with the first and second side edges 18, 20 are spaced from the straight fold line 34.

Figure 3:
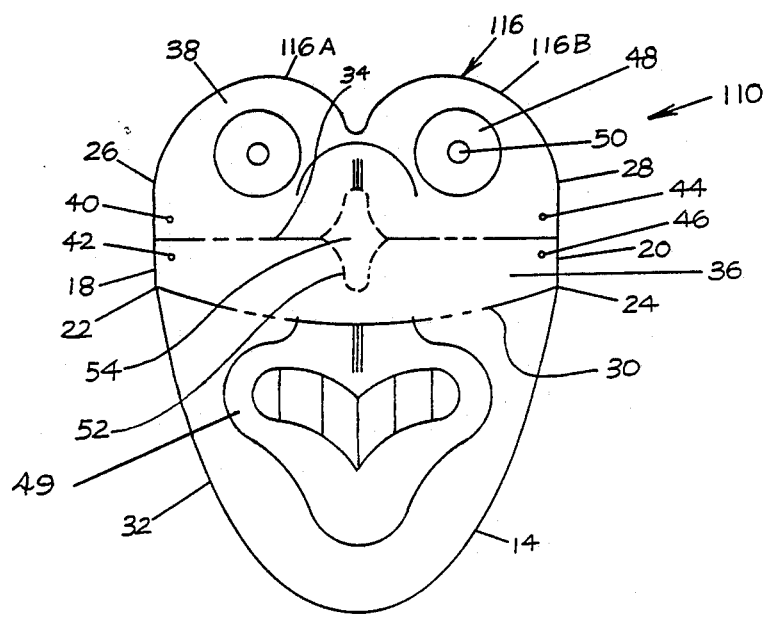
FIG. 3 is a plan view of yet another embodiment of a novel blank of the invention.

Now with reference to FIG. 3, there is shown another embodiment of a cap blank, generally denoted as the numeral 110, which is similar in most respects to the cap blank 10 of FIGS. 1 and 2. Therefore, for the sake of brevity, similar elements between the cap blank 110 and cap blank 10 are denoted by identical numerals in FIG. 3 and a description thereof will not be repeated. The cap blank 110 differs from the cap blank 10 mainly in peripheral configuration. In the cap blank 110, the second end edge 116 is configured with two arcuate portions 116A, 116B which are equally spaced to opposite lateral sides of the imaginary bisecting centerline of the second end edge 116. Thus, at least a portion of the second end edge 116 is spaced a greater distance from the straight fold line 34 than the distance by which any portion of the arcuate fold line 30 is spaced from the straight fold line 34. The cap blank 110 includes indicia 48 on the front panel 38 and different indicia 49 on the visor 32. The indicia 48 and indicia 49 cooperate or mate when the cap blank 110 is folded to form a cap/mask 112 (see FIGS. 7 and 8) to form a complete unitary design. Toward this objective, the indicia 49 terminates at about the arcuate fold line 30 and the indicia 48 terminates at a distance from the straight fold line 34 about equal to the distance between the arcuate fold line 30 and straight fold line 34. As can be best seen in FIGS. 7 and 8, the termination of the indicia 49 mates in alignment with the termination of the indicia 48 such that the indicia 48 and indicia 49 cooperate at the arcuate fold line 30 when the blank 110 is folded to form the cap/mask 112 to form the complete unitary design. This configuration can be used in an application wherein the invention can be worn as a cap (see FIG. 6) or mask 112 (see FIG. 9) and can represent, for example, a sports team mascot or the like. In this event, indicia 48 printed on the mask/cap front panel 38 represents eyes and a portion of a nose or bill fo the mascot, and the indicia 49 printed on the visor portion 32 can be decorated to represent the other portion of the nose, or bill of the mascot. For example, the mascot for the University of Louisville in Louisville, Ky. is a cardinal bird. In this case, the cap/visor 112 can be decorated to resemble the head of a cardinal with the indicia 48 on the front panel representing the eyes and upper portion of the bird's bill and the indicia 49 on the visor portion 32 representing the lower or remaining portion of the bird's bill. Advantageously, the blank 110 is formed to be selectively worn as a mask by including closely spaced perforations 52 formed through the blank 110 defining a parallelogram 54 shaped area with two of the opposite corners of the parallelogram on the straight fold line 34 and the other two of the opposite corners of the parallelogram on an imaginary bisecting centerline of the straight fold line 34 and spaced to opposite lateral sides of the straight fold line 34. In addition, appropriate holes 50 can be formed through the front panel 38 to allow the person wearing the mask to see. As will hereinafter become more clear in reference to the discussion of FIGS. 7 and 8, the material of the parallelogram shaped area 54 will be removed to provide a clearance for the bridge of a wearer's nose in the event the cap/mask 110 is worn as a mask over the wearer's face.

With reference now to FIGS. 4, 5, and 6, there is shown the cap 12. To form the cap 12 from the blank 10, the intermediate portion 36 of the blank 10 is folded upwardly about the straight fold line 34 to overlay the exterior surface of the front panel portion 38 of the blank 10, and the visor portion 32 is folded in the opposite direction or downwardly about the arcuate fold line 30 to project outwardly away from the outside or exterior surface of the front panel portion 38. When this is done, the aperture 40 of the first aperture pair is in registration with the other aperture 42 of the first aperture pair, and the aperture 44 of the second aperture pair is in registration with the other aperture 46 of the second aperture pair. When the visor portion 32 is folded downwardly about the arcuate fold line 30, the intermediate portion 36 and front panel portion 38 are formed into a curve corresponding to the curvature of the arcuate fold line 30 such that the intermediate portion 36 is on the concave exterior side of the front panel portion 38. An elastic headband 56 is affixed to the cap 10 by threading one end through the registered aperture 40, 42 of the first aperture pair and by threading the other end through the registered apertures 44, 46 of the second aperture pair. The opposite ends of the elastic headband 56 are then secured in place so as not to pull out of the apertures by various means such as a fastener (not shown) or a knot (not shown). When the cap is placed on the wearer's head, the concave side of the front panel 38 is the headband and is placed against the wearer's forehead with the visor projecting outwardly above the wearer's eyes and the elastic headband 56 encompassing the wearer's head to hold the cap 12 in place.

With reference to FIG. 9, there is shown the cap 112 worn as a mask. To form the mask 112 from the blank 110, the intermediate portion 36 of the blank 110 is folded upwardly about the straight fold line 34 to overlay the exterior surface of the front panel portion 38 of the blank 110 and the visor portion 32 is folded in the opposite direction or downwardly about the arcuate fold line 30 to project outwardly from the outside or exterior surface of the front panel portion 38, and the elastic headband 56 is attached to the mask 112 as discussed above in regard to the cap 12. The parallelogram shaped area 54 defined by the perforations 52 is punched out or removed to form a clearance notch in the center of the intermediate portion 36 and front panel portion 38 beneath the visor portion 32 and centered on the imaginary bisecting centerline of the visor portion 32 for receiving the bridge of the wearer's nose. When the mask 112 is placed on the wearer's head, the concave side of the front panel 38 beneath the visor portion 32 will be against the wearer's cheekbones below the eyes, with the visor portion 32 projecting outwardly below the wearer's eyes, and the front panel portion 38 extending upwardly in front of the wearer's eyes. The mask 112 can, of course, also be worn as a visored cap by merely positioning it such that concave interior side of the front panel portion 38 is against the wearer's forehead. The elastic headband 56 encompasses the wearer's head to hold the mask/cap 112 in place.

The foregoing detailed description is given primarily for clearness of understanding and no unnecessary limitations are to be understood therefrom for modifications will become obvious to those skilled in the art and may be made without departing from the spirit of the invention and scope of the appended claims.

I claim:

1. A flexible blank for a visored cap comprising:
   a first end edge having two terminal ends;
   a second end edge opposite the first end edge, the second end edge having two terminal ends;
   the first end edge being in alignment with the second end edge such that an imaginary bisecting centerline of the second end edge is in alignment with an imaginary bisecting centerline of the first end edge, and each of the terminal ends of the first end edge being in alignment with a different one of the terminal ends of the second end edge;
   first and second side edges, the first side edge interconnecting one of the terminal ends of the first end edge and the aligned one of the terminal ends of the second end edge, and the second side edge interconnecting the other one of the terminal ends of the first end edge and the aligned other one of the terminal ends of the second end edge;
   an arcuate fold line having two terminal ends extending between the first and second side edges convexly facing the first end edge with an imaginary bisecting centerline of the arcuate fold line being in alignment with the imaginary bisecting centerline of the first end edge, one terminal end of the arcuate fold line intersecting the first side edge and the other terminal end of the arcuate fold line intersecting the second side edge; and,
   a straight fold line having two terminal ends located between the second end edge and the arcuate fold line extending between the first and second side edges, one terminal end of the straight fold line intersecting the first side edge and the other terminal end of the straight fold line intersecting the second side edge, and an imaginary bisecting centerline of the straight fold line being in alignment with the imaginary bisecting centerlines of the first end edge, the second end edge, and the arcuate fold line, the intersection of one terminal end of the straight fold line with the first side edge being spaced between the terminal end of the first end edge and an aligned terminal end of the second end edge along the first side edge, and the intersection of the other terminal end of the straight fold line with the second side edge being spaced between the terminal end of the first end edge and an aligned terminal end of the second end edge along the second side edge.

2. The flexible blank of claim 1, wherein at least a portion of the second end edge is spaced a greater distance from the straight fold line than the distance by which any portion of the arcuate fold line is spaced from the straight fold line.

3. The flexible blank of claim 1, wherein the intersections of the terminal ends of the second end edge with the first and second side edges are spaced a greater distance from the straight fold line than the distance by which the intersections of the arcuate fold line with the first and second side edges are spaced from the straight fold line.

4. The flexible blank of claim 3, further comprising first indicia on the blank between the straight fold line and the second end edge representing a portion of a unitary design, and second indicia on the blank between the arcuate fold line and first end edge representing the other portion of the unitary design.

5. The flexible blank of claim 1, wherein the intersections of the terminal ends of the second end edge with the first and second side edges are spaced from the straight fold line by a distance equal to the distance by which the intersections of the arcuate fold line with the first and second side edges are spaced from the straight fold line.

6. The flexible blank of claim 1, wherein the first end edge is an arcuate edge in concave aligned facing relationship with the second end edge.

7. The flexible blank of claim 1, wherein the second end edge is an arcuate edge in concave aligned facing relationship with the first end edge.

8. The flexible blank of claim 1, wherein the intersection of the arcuate fold line with the first side edge coincides with the intersection of one of the terminal ends of the first end edge with the first side edge, and the intersection of the arcuate fold line with the second side edge coincides with the intersection of the other one of the terminal ends of the first end edge with the second side edge.

9. The flexible blank of claim 1, wherein the first and second side edges are straight edges parallel with each other, and parallel to the imaginary bisecting centerline of the straight fold line.

10. The flexible blank of claim 1, further comprising:
a first pair of apertures formed through the blank proximate the first side edge, the apertures of the first pair being spaced to opposite sides of the straight fold line;
a second pair of apertures formed through the blank, proximate the second side edge, the apertures of the second pair being spaced to opposite sides of the straight fold line; and,
an imaginary centerline extending between one of the apertures of the first pair and one of the apertures of the second pair being parallel to the straight fold line, and an imaginary centerline extending between the other one of the apertures of the first pair and the other one of the apertures of the second pair being parallel to the straight fold line.

11. The flexible blank of claim 1, further comprising perforations formed through the blank defining a parallelogram shape with two of its opposite corners on the straight fold line and the other two of its opposite corners on the imaginary bisecting centerline of the straight fold line and on opposite lateral sides of the straight fold line.

12. A visored cap to be worn on a person's head comprising a continuous flexible blank having a first end edge and having two terminal ends, a second end edge opposite the first end edge, the second end edge having two terminal ends, wherein an imaginary bisecting centerline of the first end edge is in alignment with an imaginary bisecting centerline of the second end edge, each of the terminal ends of the first end edge being in alignment with a different one of the terminal ends of the second end edge, first and second side edges, the first side edge interconnecting one of the terminal ends of the first end edge and the aligned one of the terminal ends of the second end edge, and the second side edge interconnecting the other one of the terminal ends of the first end edge and the aligned other one of the terminal ends of the second end edge, an arcuate fold line having two terminal ends extending between the first and second side edges convexly facing the first end edge with an imaginary bisecting centerline of the arcuate fold line in alignment with an imaginary bisecting centerline of the first end edge, one terminal end of the arcuate fold line intersecting the first side edge and the other terminal end of the arcuate fold line intersecting the second side edge, the arcuate fold line and the first end edge cooperating to define a visor portion of the cap between the arcuate fold line and the first end edge, and a straight fold line having two terminal ends located between the second line edge and the arcuate fold line extending between the first and second side edges, one terminal end of the straight fold line intersecting the first side edge and the other terminal end of the straight fold line intersecting the second side edge, an imaginary bisecting centerline of the straight fold line being in alignment with the imaginary centerlines of the first end edge, the second end edge, and the arcuate fold line, the intersection of one terminal end of the straight fold line with the first side edge being spaced between the terminal end of the first end edge and an aligned terminal end of the second end edge along the first side edge, and the intersection of the other terminal end of the straight fold line with the second side edge being spaced between the terminal end of the first end edge and an aligned terminal end of the second end edge along the second side edge, the straight fold line and the arcuate fold line cooperating to define an intermediate portion therebetween, and the straight fold line and the second end edge cooperating to define a front panel portion of the cap therebetween wherein the intermediate portion is folded upwardly about the straight fold line to overlay the outside surface of the front panel portion and the visor portion is folded downwardly about the arcuate fold line to form a curved visor projecting outwardly from the outside surface of the front panel.

13. The cap of claim 12, further comprising perforations formed through the blank defining a parallelogram shape with two of its opposite corners on the straight fold line and the other two of its opposite corners on the imaginary bisecting centerline of the straight fold line, and on opposite lateral sides of the straight fold line, the blank material enclosed by the parallelogram shape defined by the perforations being removable defining coinciding notches in the intermediate portion and front panel portions to receive the bridge of the nose of the person wearing the cap.

14. The cap of claim 13, further comprising:
first indicia on the front panel portion of the cap representing a portion of a unitary design; and
second indicia on the visor portion of the cap representing the other portion of the unitary design;
whereby the first indicia mates with the second indicia to form the complete unitary design at the arcuate fold line.

15. The cap of claim 14, wherein:
the first indicia terminates at a distance from the straight fold line about equal to the distance between the straight fold line and arcuate fold line; and,
the second indicia terminates at about the arcuate fold line;
whereby the termination of the first indicia mates in alignment with the termination of the second indicia such that the first indicia and second indicia cooperate at the arcuate fold line to form the complete unitary design.

* * * * *